United States Patent [19]

van't Hooft et al.

[11] Patent Number: 4,881,937

[45] Date of Patent: Nov. 21, 1989

[54] METHOD OF TREATING A PART OF THE BODY WITH RADIOACTIVE MATERIAL AND A TROLLEY FOR USE THEREIN

[75] Inventors: Eric van't Hooft, Gezichtslaan 16, 3956 BB Leersum; Libbe van Zwol, Leersum, both of Netherlands

[73] Assignee: Eric van't Hooft, Netherlands

[21] Appl. No.: 71,835

[22] Filed: Jul. 10, 1987

[30] Foreign Application Priority Data

Jul. 10, 1986 [NL] Netherlands ............................ 8601808

[51] Int. Cl.⁴ ........................ A61M 37/04; A61N 5/10; G21F 5/20
[52] U.S. Cl. ....................................... 600/3; 250/497.1
[58] Field of Search ............................... 600/1, 3, 6, 7; 250/497.1

[56] References Cited

U.S. PATENT DOCUMENTS

| | | | |
|---|---|---|---|
| 1,953,915 | 4/1934 | Burgett et al. | 138/131 |
| 2,904,272 | 9/1959 | Barett . | |
| 3,669,093 | 6/1972 | Sauerwein et al. | 600/7 |
| 3,861,380 | 1/1975 | Chassagne et al. | 250/497.1 |
| 4,150,298 | 4/1979 | Brault et al. | 250/497.1 |
| 4,574,196 | 3/1986 | Kampf | 250/497.1 |
| 4,631,415 | 12/1986 | Sauerwein et al. | 600/1 |
| 4,692,628 | 9/1987 | Sauerwein et al. | 250/497.1 |
| 4,733,653 | 3/1988 | Leung et al. | 600/1 |

FOREIGN PATENT DOCUMENTS

152124 8/1984 European Pat. Off. .
1127863 9/1968 United Kingdom .

*Primary Examiner*—Kyle L. Howell
*Assistant Examiner*—John C. Hanley
*Attorney, Agent, or Firm*—Griffin, Branigan & Butler

[57] ABSTRACT

There is provided an apparatus for effecting radioactive therapy in an animal body. A radioactive source assembly is disposed in a source channel, and a test assembly is disposed in a test channel. A source connecting tube is attached to the source channel and to a connector, and a test connecting tube is attached to the test channel and to the connector. A guide transfer tube is connected to the connector and an other end thereof is disposable at the site in an animal body intended for therapy. A source assembly transport thread is connected to the source assembly and a test assembly transport thread is connected to the test assembly. A source drive means is connected to an other end of the source transport thread and a test drive means is connected to an other end of the test transport thread. The source drive means and the test drive means are operable such that alternatingly the source assembly and the test assembly may be moved from the respective channels and through the guide transfer tube to the site of intended therapy. With this arrangement, the movement of the test assembly to the site of intended therapy is comparable with the movement of the source assembly to the site of intended therapy, whereby the correct positioning of the source assembly at the site of intended therapy is confirmable.

19 Claims, 3 Drawing Sheets

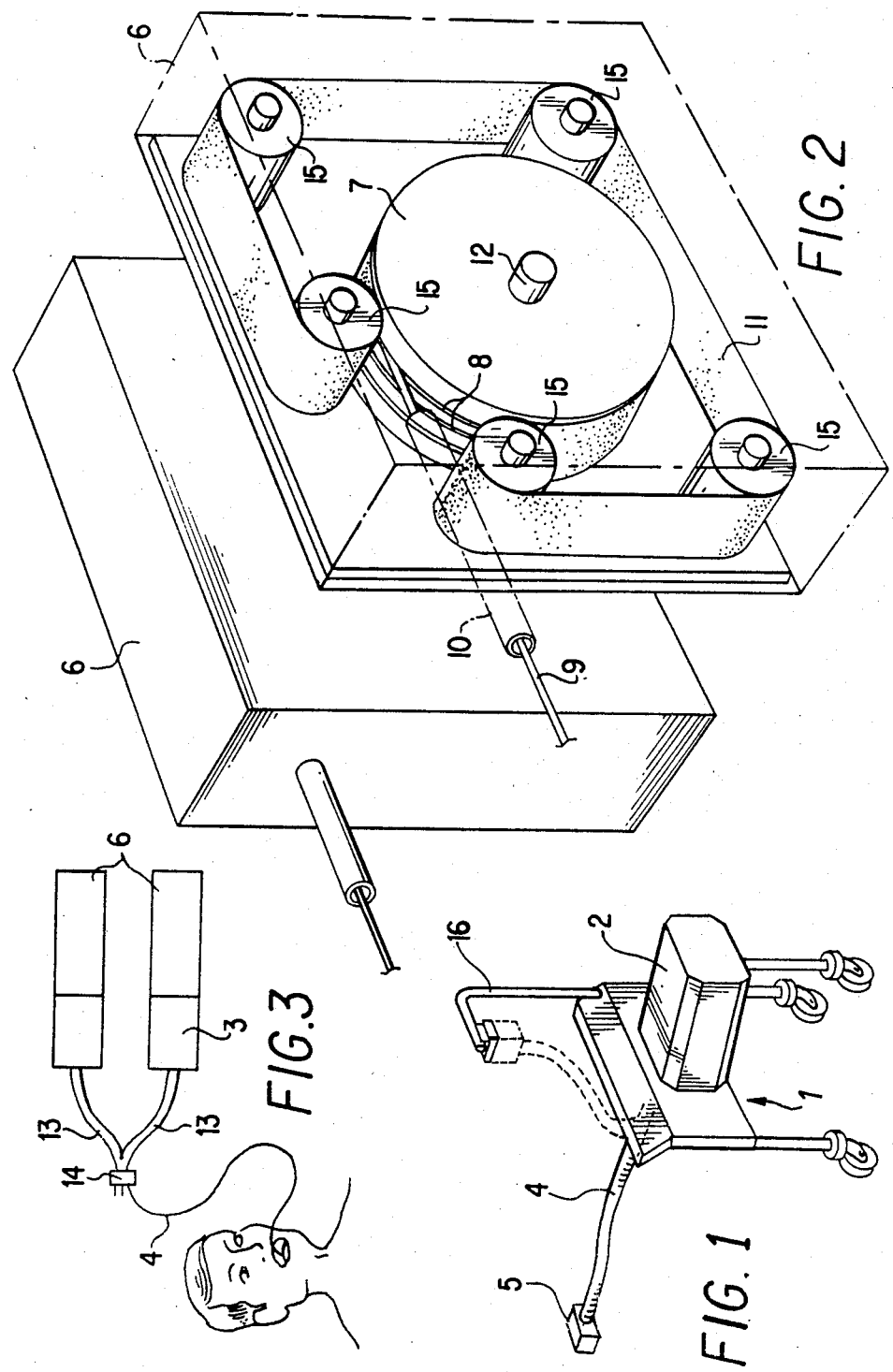

METHOD OF TREATING A PART OF THE BODY WITH RADIOACTIVE MATERIAL AND A TROLLEY FOR USE THEREIN

FIELD OF THE INVENTION

This invention relates to the treatment of a part of the body with radioactive material. It can be stated in general in respect of the treatment of a part of the body with radioactive material that two types of radiation can be used, i.e. a radiation for a short period of time at a high dose rate (HDR) and one for a longer period of time at a low dose rate (LDR). This first treatment method is employed among other things for treating lung cancer, whereas the second method is used mainly for treating breast cancer, cervical cancer and the like. The present patent application, however, concerns more in particular the first mentioned method (HDR). It will be clear that application of the subject matter according to the present invention to the second method (LDR) is not excluded.

The present invention relates more in particular to a method of treating a part of the body of a patient with radioactive material, in particular lungs or other internal organs, in which method an at least partly flexible tube is introduced into the target area, after which the radioactive material contained in a shielding block is moved from said shielding block communicating with said tube, by means of a drive mechanism arranged behind said shielding block, through said hose to the target area.

BACKGROUND OF THE INVENTION

In such a method disclosed in U.S. Pat. No. 3,669,093, the front end of the tube is placed in position as best as can be done, after which the transport member disposed behind the shielding block transports the radioactive material to the target area. During this transport, only a check of the end positions of the transport thread takes place by checking the place of the end of the transport thread by means of two spaced apart photoelectric cells.

It will be clear that this system offers no guarantee whatever for the arrival in the target area of the radioactive material present at the front end of the thread; for instance, a kink may occur in the tube during its movement via e.g. the windpipe to the target area, in this case the lungs.

SUMMARY OF THE INVENTION

It is an object of the present invention to remove this drawback.

To this effect, the above described method is characterized in that, prior to moving the radioactive material to the target area, first a dummy is moved to target area and its position is checked e.g. by means of an X-ray image intensifier.

The accuracy in respect of the arrival in the target area can be improved in that for the orientation use is made of a detection or setting point situated behind the shielding block as viewed in the direction of displacement of the radioactive material.

In a further elaboration of the present invention, when use is made of a hollow needle to be introduced in the part of the body to be treated, said needle being connectable to said tube, said detection point may be situated near the rear end of said needle.

Besides, when use is made for driving the transport thread of a drivable disc provided with a spiral groove adapted for receiving therein the required transport thread length, use can be made of a cylindrical disc on the outer circumference of which said grooves are provided, with an endless tensioning belt being provided around a major portion of said disc, thereby achieving a proper transport thread and avoiding slip.

To ensure that no errors are made when changing the tube length, one or more of the tubes employed consists of a helically wound wire having adjoining windings, a pull wire extending therealong, with the ends of said spring and said pull wire being attached to coupling portions, and said windings and pull wire being embedded in a synthetic plastics sheath.

By driving the disc with a stepping motor, a highly accurate positioning of the radioactive material can be obtained in a simple manner.

The present invention further relates to a trolley for use in the performance of the above described method, said trolley being provided with a shielding block having at least one curved channel behind which there is arranged a transport mechanism, said trolley being characterized in that beside said transport mechanism for transporting radioactive material, there is arranged a second transport mechanism for transporting a dummy, and the transport channels for the transport threads with radioactive material, and the dummy, respectively, being combined ahead of the detection point. Naturally, a plurality of drive mechanism for transporting radioactive sources can be arranged side by side.

When the transport mechanism is provided with a drivable disc having a spiral groove, with a transport thread being received in said groove, the front end of said thread being adapted for coaction with radioactive material, such as known from Applicant's Dutch patent application 8400108, said groove may be provided on the cylindrical circumference of said disc and a tensioning belt or drive mechanism may be provided around the circumference of said disc.

For the sake of completion, it is observed that Applicant's prior Dutch patent application 84,00108 (corresponding with European patent application 85200018.1 or U.S. Pat. No. appl. 1017036) discloses a method and an apparatus for treating a part of the body with radioactive material, with the detection point likewise being disposed near the target area. However, compressed air is used therein, which implies that a number of additional provisions have to be made.

By driving the disc or tensioning belt by means of a stepping motor with feedback, a highly accurate, reproducible location can be obtained.

As particularly important advantages of the method and apparatus according to the present invention can be mentioned.

1. Safety: An automatic test run through the applicator checks all connections and reports the position of any kinks or unsuitable curvatures, which could result in the active source jamming during treatment. In the event of this test failing, source transfer is not possible.

2. Simulation: The dummy can be used to simulate the programmed source dwell positions under fluoroscopy.

3. Measuring: The dummy can be used for measuring skin entry and exit points or visible tumour borders or markers. This helps the user to program his machine accurately and fast.

For the sake of completion, reference is made to Swiss Pat. No. 519,918 corresponding with U.S. Pat.

No. 3,861,380, which also concerns the use of a dummy; however, this is coupled and uncoupled by hand. It does not concern at all an accurate check by means of a detection or setting point arranged behind the shielding block.

BRIEF DESCRIPTION OF THE DRAWINGS

One embodiment of the apparatus for treating a part of the body with radioactive material will now be described, by way of example, with reference to the accompanying drawing, in which:

FIG. 1 is a perspective view of an embodiment of a trolley for use in the treatment of a part of the body of a patient with radioactive material;

FIG. 2 is a perspective detail view of the apparatus of FIG. 1;

FIG. 3 is a diagrammatic view of the treatment of a part of the body of a patient with radioactive material.

DETAILED DESCRIPTION OF THE INVENTION

Figure 4:
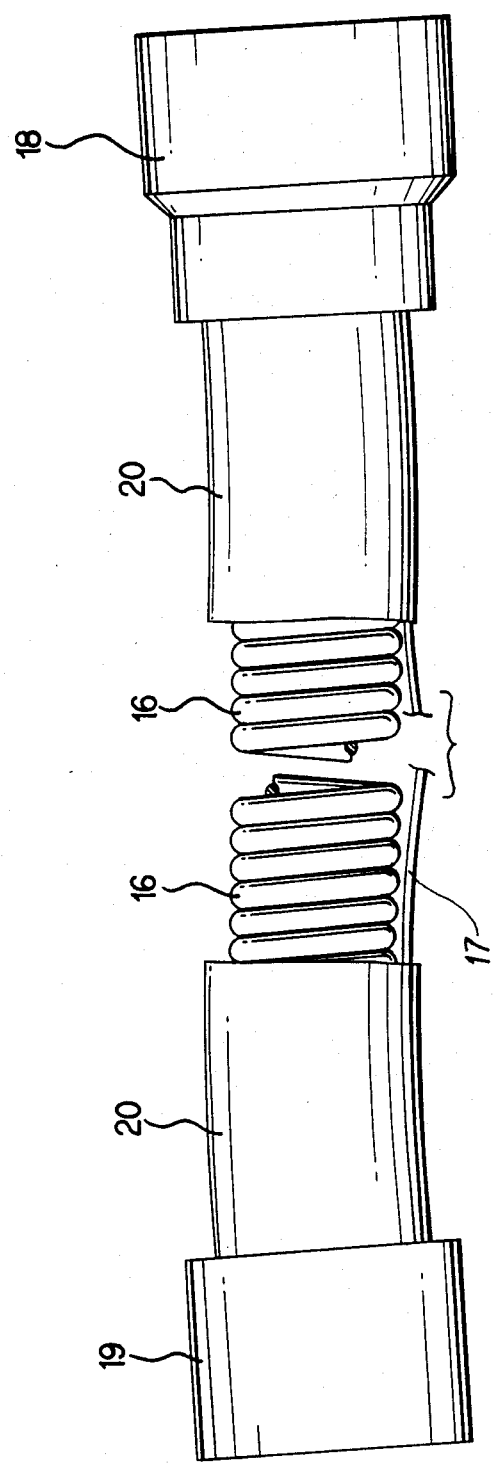
FIG. 4 is an enlarged perspective view of the guide tube used in the apparatus shown in FIGS. 1-3, with a portion of the tube removed for clarity.

As shown in the drawing, see in particular FIG. 1, a trolley adapted for treating a patient, is provided with a movable frame generally indicated at 1. Said frame supports a housing 2 accommodating a shielding block 3. Said shielding block contains a known per se curved channel for receiving therein radioactive material. However, this is extensively described in Applicant's prior Dutch patent application 84,00108, so that a further description thereof can be dispensed with.

Figure 5:
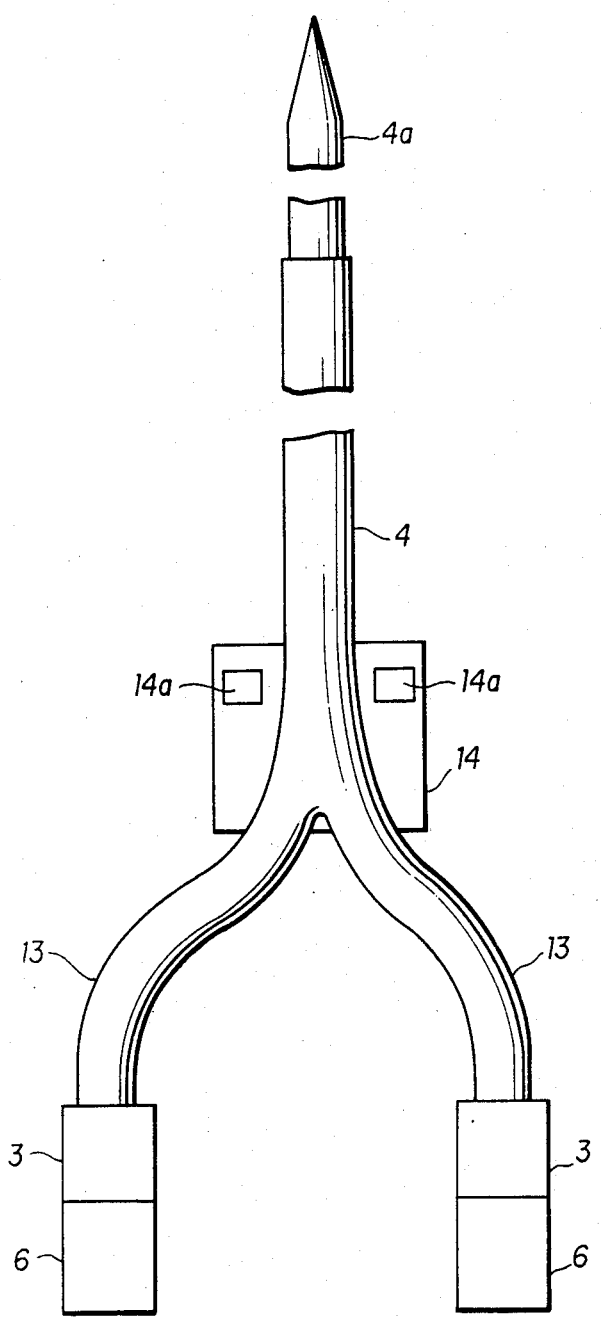
FIG. 5 is an enlarged diagrammatic view of part of FIG. 3, showing ore detail of the detector which serves as a connector for tubes of the apparatus and the use of a hollow needle as part of the guide tube.

To the front end of the housing 2 connects a guide tube 4 provided in the present case with connector 5 which, when not being used, can be suspended from a bracing rod 16. Said connector can be connected in the same manner as in Applicant's prior Dutch application to a counter-connector. In some cases, however, the front end of said guide tube 4 will be fitted with a hollow "needle" 4a (partially shown in FIG. 5) insertible into the part of the body to be treated. In the present case, as shown in FIG. 3, two shielding blocks 3 are arranged each together with a drive mechanism 6, disposed behind each shielding block on a support foot (not shown). Each drive mechanism essentially consists of a cylindrical disc 7 on the outer surface of which there is provided a helical groove 8, adapted to receive a transport thread 9. Said transport thread 9 is taken off disc 7 by means of a tubular guide 10 whose outwardly extending end links up with the channel, not further indicated, through shielding block 3.

Transport thread 9 is retained accurately and slip-free in grooves 8 of the transport disc 7 by means of a tensioning belt 11 wrapped about the rollers 15, said belt 11 embracing said transport disc 7 through about 30020 . Transport disc 7 is driven by a diagrammatically shown stepping motor 12. For the sake of completion, it is observed that at least one of rollers 15 is springbiased.

The channels in each of the shielding blocks 3 connect to a connecting tube 13 (see FIG. 3) which are combined to a single guide tube, i.e. tube 4.

In downstream direction beyond the junction of the two connecting tubes 13, there is arranged a a detector 14 which serves as a connector for tubes 13 and 4 and contains a detecting device, such as a photoelectric cell 14a (see FIG. 5), serving as point of reference or zero point setting, and which is therefore coupled to the stepping motor 12.

As already observed in the above, the apparatus is provided with a shielding block 3 and two drive mechanisms 6. The shielding block 3 is filled with a dummy used at the beginning of the treatment of a patient (see FIG. 3) to check whether the guide tube 4 has been transported into the target area without kinks. To this effect, the dummy is advanced by means of the stepping motor from the shielding block 3 in question, with the photoelectric cell 14 or other detector serving as point of reference for the stepping motor. Besides the same shielding block 3 there is arranged, having its own transport unit 6, a further shielding block 3 containing a radioactive preparation. However, it will be clear that the apparatus may also be fitted with a different number of transport mechanisms, or with a different number of shielding blocks with radioactive material.

In order to prevent deformations of the guide tube 4, as a result of which the radioactive material could be moved to the wrong place, the guide tube, as shown in FIG. 4, consists of a metal spring having adjoining windings 16. A pull wire 17 keeping said windings in adjoining relationship is affixed to corresponding male and female coupling portions 18, 19, which are known per se. Said windings and pull wire are embedded on all sides in a synthetic plastics sheath 20.

Such a tube construction ensures that the length thereof always remains equal, so that no errors can be made in moving the radioactive sources to their destination.

The apparatus according to the present invention is especially suitable for treating a part of the body of a patient according to the HDR method: the apparatus can be brought to near the patient, the radioactive preparation can then be brought accurately into the target area, with the apparatus itself being of very simple construction.

We claim:

1. In an apparatus for effecting radioactive therapy in an animal body wherein the apparatus has a radioactive source assembly disposed in a source channel, a guide tube connected at a first end to said source channel and a second end being disposable in the animal body for the intended therapy, a source assembly transport thread connected to the source assembly and to a source assembly drive means for driving the source assembly from the source channel and towards the said second end of the guide tube, the improvement comprising a test assembly disposed in a test channel, a connector tube connected at a first end to said test channel and at a second end to a connector disposed in said guide tube, wherein a juncture is formed at said connector between said guide tube and said connector tube, a test assembly transport thread attached at one end to said test assembly and at the other end to a test assembly drive means for driving the test assembly from the test channel, through the connector tube and connector, and towards said second end of the said guide tube, whereby the source assembly and the test assembly are alternatingly drivable toward the second end of the guide tube, and a detector means for detecting the presence of the test assembly, or the source assembly in the guide tube between the juncture and the second end of the guide tube.

2. The apparatus of claim 1 wherein the test assembly is of substantially the same shape as the source assembly.

3. The apparatus of claim 1 wherein the test assembly has no radioactive material therein.

4. The apparatus of claim 1 wherein the said source assembly drive means and said test assembly drive means includes a motor means for driving said drive means.

5. The apparatus of claim 4 wherein the motor means is a stepping motor.

6. The apparatus of clam 5 wherein separate stepping motors are operably connected to said source assembly drive means and said test assembly drive means.

7. The apparatus of claim 1 wherein the said detector means is disposed in said connector means.

8. The apparatus of claim 1 wherein the said guide tube is connected at its said other end to an implant needle which is disposable at the site of intended therapy and the test assembly and source assembly are passable into said needle.

9. The apparatus of claim 1 wherein the said detector means comprises a photodetector.

10. The apparatus of claim 1 wherein the source drive means comprises:
   (a) a cylindrical disc having on its outer circumferential surface a groove spirally disposed around said surface and the said source transport thread is disposed in said groove;
   (b) an endless belt disposed on contacting means for contacting the belt against a major portion of the said surface and for retaining the said source transport thread in said groove and
   (c) a tubular guide means for passing the said source transport thread to said source channel.

11. The apparatus of claim 10 wherein the said contacting means is a series of rollers upon which the endless belt rolls and said rollers are disposed in relation to said surface such that the said endless belt is in contact with said surface and is moved around said major portion of said surface by movement of said cylindrical disc.

12. The apparatus of claim 11 wherein the said major portion of the said surface is at least about 300° of arc.

13. The apparatus of claim 1 wherein said guide tube has disposed thereabout a helically wound metal spring wire and a longitudinally disposed pull wire adjacent said spring wire having ends respectively affixed at the ends of the guide tube wherein the said spring wire and pull wire prevent deformation of the said guide tube.

14. The apparatus of claim 13 wherein the said spring wire and pull wire are embedded in a plastic sheath.

15. The apparatus of claim 1 wherein the said test assembly is made of a material which is x-ray imagable.

16. The apparatus of claim 1 wherein the test drive means comprises:
   (a) a cylindrical disc having on its outer circumferential surface a groove spirally disposed around said surface and the said test transport thread is disposed in said groove;
   (b) an endless belt disposed on contacting means for contacting the belt against a major portion of the said surface and for retaining the said test transport thread in said groove and
   (c) a tubular guide means for passing the said test transport thread to said source channel.

17. The apparatus of claim 16 wherein the said contacting means is a series of rollers upon which the endless belt rolls and said rollers are disposed in relation to said surface such that the said endless belt is in contact with said surface and is moved around said major portion of said surface by movement of said cylindrical disc.

18. The apparatus of claim 17 wherein the said major portion of the said surface is at least about 300° of arc.

19. The apparatus of claim 1 wherein the said source channel and the said test channel are disposed in a shielding block.

* * * * *